United States Patent
Schnell et al.

(10) Patent No.: US 7,446,531 B2
(45) Date of Patent: Nov. 4, 2008

(54) MAGNETIC RESONANCE SYSTEM WITH BUILT-IN DEPLOYABLE/RETRACTABLE LOCAL COIL

(75) Inventors: Wilfried Schnell, Forchheim (DE); Markus Vester, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 63 days.

(21) Appl. No.: 11/687,066

(22) Filed: Mar. 16, 2007

(65) Prior Publication Data

US 2008/0129293 A1    Jun. 5, 2008

(30) Foreign Application Priority Data

Mar. 17, 2006    (DE) .................. 10 2006 012 404

(51) Int. Cl.
*G01V 3/00* (2006.01)

(52) U.S. Cl. .................. 324/318; 324/322

(58) Field of Classification Search ......... 324/300–322; 600/407–449
See application file for complete search history.

(56) References Cited

U.S. PATENT DOCUMENTS

| | | | |
|---|---|---|---|
| 5,085,219 A * | 2/1992 | Ortendahl et al. ........... | 600/422 |
| 5,548,216 A | 8/1996 | Dumoulin et al. | |
| 6,529,004 B1 | 3/2003 | Young | |
| 6,529,764 B1 * | 3/2003 | Kato et al. .................. | 600/411 |
| 7,053,620 B2 * | 5/2006 | Renz ........................... | 324/318 |
| 7,266,406 B2 * | 9/2007 | Kroeckel .................... | 600/410 |
| 2002/0138001 A1 | 9/2002 | Krocckel | |
| 2003/0076101 A1 | 4/2003 | Sakuma et al. | |
| 2005/0012502 A1 | 1/2005 | Renz | |
| 2005/0134272 A1 | 6/2005 | Roberts et al. | |

* cited by examiner

*Primary Examiner*—Brij B Shrivastav
(74) *Attorney, Agent, or Firm*—Schiff Hardin LLP

(57) ABSTRACT

A magnetic resonance system has a cylindrical patient support unit in the form of a chamber delimited by a wall with a patient bed, as well as at least one flexible flat local coil element with at least one local coil. The local coil element is attached on two opposite sides to mountings accommodated in the chamber. At least one of the mountings at one side is guided to allow movement along the chamber wall, during which manual or automatic movement the local coil element is moved from a storage position adjacent to the wall of the chamber into a position on the patient, or the local coil element attached to the patient bed is able to be moved manually from a storage position to the side or below the patient bed against a return force, into a position on the patient.

28 Claims, 2 Drawing Sheets

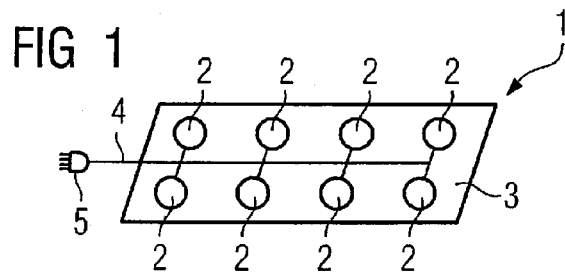
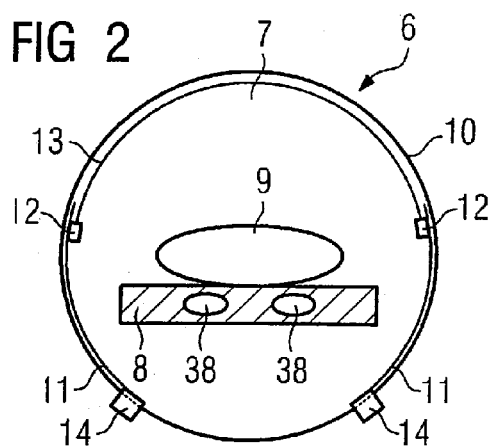
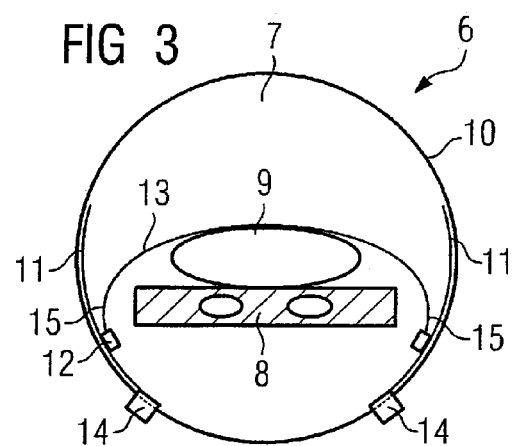
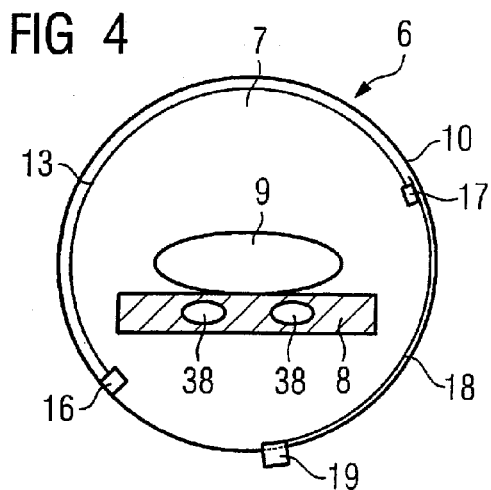
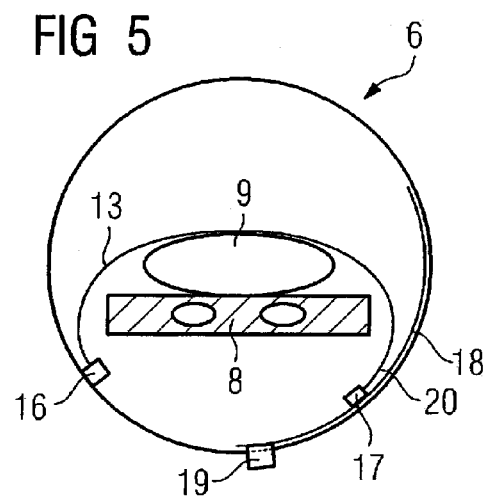

MAGNETIC RESONANCE SYSTEM WITH BUILT-IN DEPLOYABLE/RETRACTABLE LOCAL COIL

BACKGROUND OF THE INVENTION

1. Field of the Invention

The present invention relates to a magnetic resonance system, of the type having a cylindrical patient support unit in the form of a chamber delimited by a wall with a patient bed, as well as at least one flexible flat local coil element with at least one local coil.

2. Description of the Prior Art

In modern magnetic resonance systems local coils are used as reception coils in order to obtain a better resolution of images by placing them closer to the patient. for this purpose, the practice of laying the local coils directly on the patient is known. Since the coils can be placed close to the patient in this way, a high signal-to-noise ratio (SNR) is achieved. Disadvantageously, however, the process of attaching the coils to the patient is a very complex one. There is also the fact that multi-pin plug-in connections are used which are mechanically very delicate.

In a further solution local coils to be plugged into the patient bed are provided. Mountings of different sizes and in different positions, however, must be available to bring the coils very close to the patient and thereby achieve a high SNR. Again, a certain installation or de-installation time is required. Here as well the coil connectors are mechanically strained.

In other known magnetic resonance systems local coils are provided that are fixed behind the cladding, which are usually as used as the transmission antenna. As a result of their large distance from the patient, only a very low SNR is achieved, particularly in the case of slim patients for whom the antenna is far removed from the body.

United States Patent Application Publication No. 2002/0138001 A1 proposes installing a rigid local coil or local coil arrangement within the patient support unit. An actuator can be used to lower the local coil arrangement from above down onto the patient. This does not achieve good positioning on the patient. Furthermore, significant space is required for the actuator.

U.S. Pat. No. 5,548,218 discloses a local coil arrangement which has flexible wings which can be laid over a patient's body. Such a local coil arrangement, however, must first be attached to the patient.

SUMMARY OF THE INVENTION

An object of the present invention is to provide a magnetic resonance system with local coil element, meaning a coil array, such that, in a simple, space-saving and easy-to-handle construction without complex cabling, the ability to bring the local coils close to the patient and thereby an improvement in the image quality, is achieved.

This object is achieved in accordance with the invention by a magnetic resonance system of the type initially described, wherein the local coil element is attached on two opposite sides to mountings provided in the chamber, with at least one of the mountings having one side guided movably along the wall of the chamber during the manual or automatic movement, and the local coil element can be moved from a storage position adjacent to the wall of the chamber into a position on the patient, or the local coil element attached to the patient bed can be moved manually from a storage position to the side of or below the patient bed, preferably against a return force created by a return element, into a position on the patient.

In accordance with the invention, the local coil element is designed as a fixed part of the magnetic resonance system and simultaneously has a space-saving storage position. The local coils are consequently integrated into the magnetic resonance system so that tedious installation/dismantling no longer has to be undertaken. Furthermore, complicated cabling does not have to be connected each time and the terminals of the local coils are not overstressed. In the storage position the local coil element is appropriately stowed in the free space that is available anyway, and can be brought to the patient from that position, and because of the flexibility of the local coil element, it can be brought close to the patient as well. One local coil element can consequently be used for all patients. Advantageously the local coil element can be returned to its storage position by a few simple manual movements, or automatically. The patient is consequently not stressed by complicated installation and dismantling work while in the patient support unit.

The guidance of the flexible local coil element in mountings along the wall of the chamber not only achieves a simple-to-implement and space-saving device, but also the movement path along the wall of the chamber places the local coil element around the patient in a natural manner. No further complicated positioning is required. In one embodiment, the local coil element can be permanently attached on one side to the wall of the chamber at the height of the patient bed or below it, and only one mounting with any number of mounting elements can be supported to allow movement. In a second embodiment both mountings, including the mounting elements, are supported to allow movement.

Alternatively a storage position can also be selected to the side of or below the patient bed and the local coil element can be attached to the patient bed. In accordance with the invention a return element is provided that creates a return force, so that the deployed local coil element, when it is not attached, can return automatically to its storage position due to the return force. This advantageously produces an extremely simple-to-handle arrangement in which the local coil element can be brought into position on the patient through a simple manual movement and moves practically on its own back into the storage position as soon as the images have been recorded.

Different circuit arrangements can be provided for the flexible flat local coil element. Preferably, a flexible plastic material is used as carrier material in which or on which the individual local coils are arranged. Advantageously the local coils are embedded into the flexible plastic material both for protection of the coils and of the patient, so that they are isolated from environmental influences and from contact with the skin of the patient or of an operator. Regardless of whether one local coil or a number of local coils are used in the local coil element, only a single connection need be provided for data transmission. This output cable is then permanently connected by an appropriate connection to the electronics of the magnetic resonance system.

If the mountings allow movement on both sides of the patient support unit, the movable mountings can advantageously be movement-coupled. The local coil element is uniformly6 positioned on the patient from below and uniformly placed around the patient.

To guide the mountings along the wall of the chamber, a linear guide can be provided. In particular a motor can be provided in this case, through which the mobile mounting can be moved automatically in the linear guide. The operator merely has to operate a switch or such in this case to lower the local coil element and bring it into position on the patient. In a further embodiment sensors are provided on the local coil element that detect contact with the surface of the patient and through which it is thus possible to prevent too great a pressure being exerted on the patient.

Latching positions can be provided on the linear guide, at which the mountings can be latched, or the mountings can be latched at given positions along the linear guide. Consequently a step-by-step movement of the local coil element as well as a continuous movement option for the movement are provided. The latching be undertaken, for example, mechanically by deploying a locking bolt or using a friction brake.

The local coil element attached to the mountings accommodated in the chamber can be pre-tensioned so as to lie automatically on the wall of the chamber. The local coil element consequently lies flat on the wall of the chamber in this embodiment. Space requirements are thus further minimized. In addition, this prevents the local coil element from being able to hang down loosely in the patient support unit.

Expediently a holder for accommodating the local coil element attached to the patient bed can be provided in, under or to the side of the patient bed, into which the local coil element can be retracted and from which it can be deployed. The local coil element is not openly visible, when stored and is advantageously protected in its holder from outside influences.

To further facilitate a space-saving storage, the local coil element can be rolled up in the storage position. Preferably the local coil element can be moved against a return force from the storage position, with the return force being created by a return element connected to the local coil element, preferably in the form of a flexible spring, for example a torsion spring. The local coil element can then simply be pulled out from its storage position in the manner of a roller shutter, using a handle, for example, and brought into position on the patient. When the local coil element is no longer required, it simply rolls back up again as a result of the return force and disappears sideways or below the patient bed or if provided, into the holder. This means that a compact, simple-to-operate and space-saving device is implemented, which, despite its simple construction, still allows the local coil element to be accommodated in accordance with data acquisition requirements and also enables it to be positioned as close as possible to the patient.

As an alternative to the rolled-up storage position, the local coil element can be stored underneath the patient bed in an extended position, with the extended local coil element preferably also being able to be moved from its storage position against the return force of a return element, e.g., a spring or a pneumatic or hydraulic cylinder or an electrically operable, preferably piezoelectric means. In this case it is especially useful for a holder to be provided. The local coil can then be accommodated in a space-saving manner below the patient bed and, for example, pulled out using a handle and put into position on the patient. If not in use it is automatically retracted again. This alternate construction exhibits especially good space savings and ease of operation.

In a further embodiment of the invention an attachment device can be provided for attaching the local coil element to the patient bed in position on the patient. Such an attachment device can be, for example, a latch or a Velcro® fastener or a magnetic device or a hook device. Despite the return force, this provides a simple way to retain the local coil element in position on the patient. When a handle is present, a part of the attachment device or the entire attachment device can be located on the handle. This advantageously combines the two functional elements.

As an alternative to using a single coil element, at least two local coil elements attached opposite each other on the patient bed can be provided, which are able to be mechanically connected, using the aforementioned attachment device, in position on the patient. The local coil elements are pulled out to the left and the right of the patient and are connected centrally above the patient using the attachment device, for example a latch or a Velcro® fastener or a magnetic device, or a hook device.

Generally it is preferable for the local coil element to be transparent or to have cutouts (openings). This makes it easier to position the local coil precisely, since the team member or the operator can always see where the local coil element is located on the body of the patient. The local coil element consequently can be formed of a transparent plastic, or cutouts, i.e. free spaces, can be left in the areas in which no wires of the coils are accommodated, through which the surface of the patient can be seen. The cutouts also result in a weight reduction for the device.

To allow a more precise positioning of the local coil provision to be achieved, the local coil element can be designed as to be moveable in the direction of the longitudinal axis of the magnet. If necessary, a further linear guide or a number of linear guides can be provided, with which the local coil element can be moved along the center axis of the chamber. It is also possible to design the local coil element to be appropriately narrow and still be able to record images at different areas of the patient, for example at the legs or the head.

As an alternative or in addition, a number of local coil elements can be provided along over the longitudinal length of the basic field magnet. This also makes it possible to provide smaller local coil elements and still allow images to be recorded in different areas of the patient.

It is especially useful for at least one permanently installed local coil to be provided in or below the patient bed. Since the patient is accommodated on the patient bed this further local coil is naturally accommodated as close as possible to the patient. An all-round coverage is thus obtained which, when the local coil element is deployed, assures an outstanding and improved image quality.

In a further embodiment of the invention a damping element can be provided to slow the return movement of the local coil into the storage position. This damping element can be, for example, at least one braking element. In this way the local coil element is prevented during its movement, especially when it is returning to its. storage position, from making uncontrollable and undesired movements because its speed is too great. In the case of a local coil element attached to the patient bed, the damping element causes the local coil element to move back into its storage position from its position on the patient in a non-disturbing and braked manner without further need for intervention by an operator.

DESCRIPTION OF THE DRAWINGS

FIG. 1 is a basic diagram of a local coil element for use in accordance with the present invention.

FIG. 2 is a section through the patient support unit of a magnetic resonance system in accordance with a first exemplary embodiment, with the local coil element located in the storage position.

FIG. 3 is a section through the patient support unit of the magnetic resonance system according to the first exemplary embodiment, with the local coil element located in position on the patient.

FIG. 4 is a section through the patient support unit of a magnetic resonance system in accordance with a second exemplary embodiment, with the local coil element located in the storage position.

FIG. 5 is a section through the patient support unit of the magnetic resonance system according to the second exemplary embodiment, with the local coil element located in position on the patient.

DESCRIPTION OF THE PREFERRED EMBODIMENTS

Figure 6:
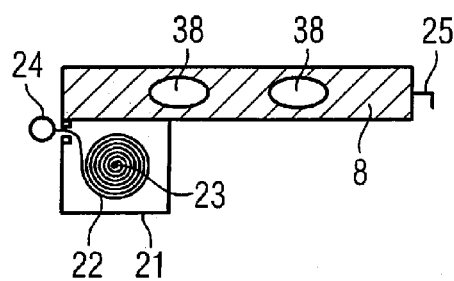
FIG. 6 is a section through a patient bed according to a third exemplary embodiment of a magnetic resonance system, with the local coil element located in the storage position.

FIG. 1 shows a basic diagram of a local coil element 1. In this diagram a number of local coils 2 are embedded into a plastic carrier 3. All local coils 2 are—also connected within the plastic carrier 3—to common cabling and electronics 4, so that the cabling and electronics 4 can be connected via a single terminal 5 (or also a number of terminals) to the corresponding cabling and electronics of the magnetic resonance system. The plastic carrier 3 is of a transparent and flexible design so that it can adapt to the form of a patient's body. As an alternative or in addition to the use of a transparent plastic carrier, provision can be made for cutouts to be provided in the plastic carrier which make the local coil element 1 lighter and allow a view of the patient during positioning.

FIG. 2 shows a section through a patient support unit 6 in the form of a chamber 7. The patient bed 8 with a patient 9 shown on it is located in the patient support unit. Linear guides 11 are provided to the left and right along the wall of the chamber 10 alongside the bed 8. Mountings 12 are guided within these linear guides 11 between which a local coil element 13 is held. The mountings 12 in this case can also feature a number of mounting elements arranged over the length of the chamber, which are each guided in a separate guide rail of the linear guide 11. The local coil element 13 is pre-tensioned, so that it lies in the storage position shown in FIG. 2 on the wall of the chamber 10. The mountings 12 can be moved within the linear guide 11 by motors 14 of which the movement is linked. If the motors 14 are activated, the mountings 12 move down along the linear guides 11 and thereby also move the flexible local coil element 13 downward. In this case either different latching positions are provided so that the local coil element 13 is able to be moved by discrete sections, or the mountings 12 can be locked within the linear guides 11 into any given position, for example mechanically by a pin. The motors 14 are controlled via a suitable control device by the operator.

FIG. 3 shows a further section through the patient support unit 6. The local coil element 13 has been moved by the movement of the motors 14 from the storage position into a position on the patient 9, so that the local coils not shown in this diagram are located as close as possible to the patient 9. Sections 15 of the local coil element 13 which are not required are now arranged below the patient bed 8, where they can be deactivated if necessary so as not to disturb the measurements. After images have been recorded, the local coil element 13 can be moved back into the storage position using the motors.

FIGS. 4 and 5 show a section through the patient support unit 6 of a second embodiment of a magnetic resonance system. In these figures the same components are identified by the same reference symbols. Here too the chamber 7 is delimited by the chamber walls 10. A patient bed 8 with a patient 9 has already been moved into the chamber 7. By contrast with the first embodiment depicted in FIGS. 2 and 3, a fixed, i.e. immovable mounting 16 is now provided, arranged for example below the patient bed 8. The local coil element 13, which is once more pre-tensioned so that it lies against the wall of the chamber 10 in its storage position, is also held in a second, mobile mounting 17 which in turn is guided in a linear guide 18. Using a motor labeled 19 the movable mounting 17 can be moved along the wall of the chamber 10 in the linear guide 18. This is again done either by an operator activating a corresponding control device or automatically. FIG. 5 again shows the patient support unit 6 of the second embodiment with the local coil element 13 in position on the patient. Here as well, the flexible local coil element 13 can be brought as close as possible to the object under examination, in this case the patient 9, by simply moving a mounting 17 along the linear guide 18. Here as well, areas 20 of the local coil element 13 not needed are located below the patient bed 8, i.e. they are able to be embodied so that they can be deactivated if necessary.

Figure 7:
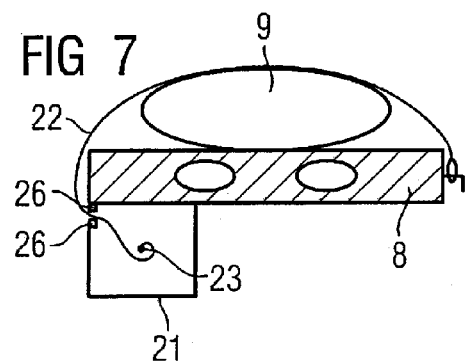
FIG. 7 is a section through the patient bed depicted in FIG. 6, with the local coil element in position on the patient.

FIGS. 6 and 7 show a section through the patient bed of a magnetic resonance system in a third embodiment. Below the patient bed 8 a holder 21 in the form of a box accommodated under the patient bed 8 is provided. In it is located, here in its stored state, a rolled-up local coil element 22. The local coil element 22 is for example attached to a torsion spring which forms the return element 23, so that with the aid of the handle 24 it can be pulled out of its holder 21. In its extended form, the local coil element 22, as shown in FIG. 7, can be laid over the patient 9, subsequently being brought into a position on the patient 9. The return element 23, that is the torsion spring shown as an example here, can roll the local coil element 22 back up into the holder 21. So that the local coil element 22 remains in its position on the patient 9, an attachment device 25 in the form of a hook device is provided. In this case a hook can protrude and can be inserted into an appropriate opening on the handle 24 of the local coil element 22, so that the local coil element 22 is held securely in the position on the patient 9. When the attachment device 25 is released again, the return element 23, here in the form of the torsion spring, attempts to pull the local coil element 22 back into the holder 21. So that this can occur in a controlled manner, two braking elements 26 can be provided at the opening in holder 21, which decelerate or attenuate the return movement of the local coil element 22. This prevents the local coil element 22 making unpredictable movements.

Figure 8:
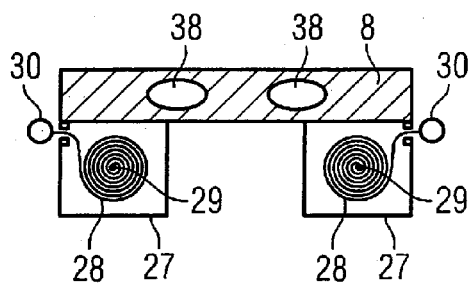
FIG. 8 is a section through a patient bed according to a fourth embodiment of a magnetic resonance system, with the local coil elements in the storage position.
Figure 9:
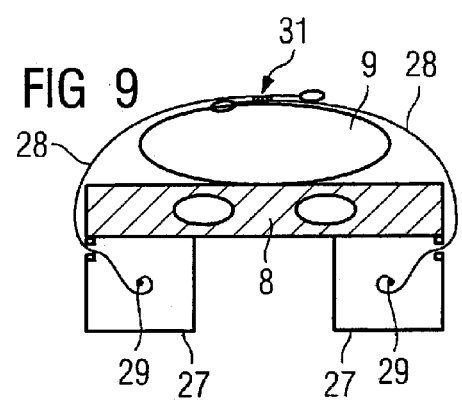
FIG. 9 is a section through the patient bed depicted in FIG. 8, with the local coil elements in position on the patient.

FIGS. 8 and 9 show a section through the patient bed 8 in a magnetic resonance system of a fourth embodiment. Here two holders 27 arranged at the same height are provided. In each of the holders 24, a local coil element 28 is attached to a return element 29, here a flexible spring for example. The local coil elements 28 in this case are around half as big as the local coil element 22 of the third embodiment. Both local coil elements are provided with a handle 30, by which for example they can be pulled by an operator against the force of the return element 29, in this case the torsion springs mentioned in the example, out of their holders 27.

If there is now a patient 9 on the patient bed 8, as shown in FIG. 9, the complementary local coil elements 28 can be positioned on the patient 9 by pulling them out. The local coil elements 28 can be fastened to each other above the patient 9 with the aid of a means of attachment 31, embodied here as a Velcro® fastener, so that they remain in position on the patient. In this embodiment too damping means can be provided to prevent the local coil elements 28 moving back into their holders 27 too quickly.

Figure 10:
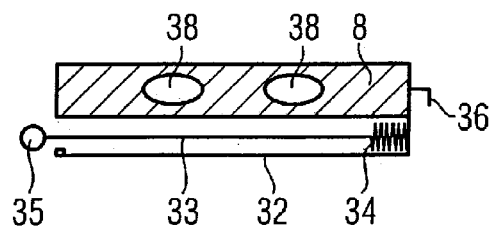
FIG. 10 is a section through the patient bed according to a fifth exemplary embodiment of a magnetic resonance system.
Figure 11:
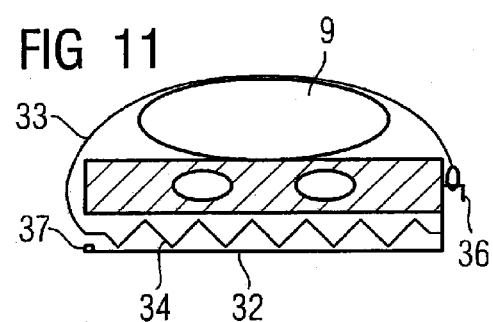
FIG. 11 is a section through the patient bed depicted in FIG. 10, with the local coil element in position on the patient.

A fifth embodiment is shown in FIGS. 10 and 11. Again the section through a patient bed 8 is shown. This time a lengthwise holder 32 under the patient bed is provided, in which a local coil element 33 attached to a linearly-acting return element 34 e.g. in the form of a spring, e.g., a coil spring, is shown in its storage position. At its end that protrudes from the holder 32 the local coil element 33 is again provided with a handle 35. The local coil element 33 can be pulled out of the holder 32 with the aid of the handle against the return force of the linear return element 34 and, as shown in FIG. 11, be brought into a position on a patient 9. In this case a means of attachment device 36 in the form of a hook device is again provided, with a hook able to be hooked into a hole on the handle. Optional damping in the form of a braking element 37 prevents the local coil element 33 from returning too quickly into the holder 32 when the attachment device 36 is released.

Naturally the fifth embodiment can also be modified with the local coil elements stored stretched under the bed so that two local coil elements of around half the length are provided.

In all embodiments further local coils 38 are provided in or under the bed under the patient 9. These too are thus located in the immediate vicinity of the patient 9, so that an outstanding signal-to-noise ratio is achieved and all-round coverage is provided.

With all exemplary embodiments it is possible for the local coil elements to be embodied along the longitudinal axis of the patient support unit. Further linear guides can typically be provided for this purpose. A slider rail is also conceivable. This enables smaller local coil elements to be used while still recording images of different areas of a patient. As an alternative or in addition, a number of local coil elements can be provided that are distributed along the length of the patient bed or the patient support unit.

In the third, fourth and fifth embodiments (FIGS. 6+7, 8+9 and 10+11) the return element 23, 29 or 34 can be replaced by a spring, of by other elements that exert a force, such as a pneumatic or hydraulic drive or cylinder or electrical or piezo motors for example. These too can exert an appropriate return force.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance system comprising:
   a magnetic resonance data acquisition unit configured to interact with a patient, having a chamber defined by an interior chamber wall, and having a patient bed configured to receive a patient thereon;
   a flexible local RF coil element comprising at least one local RF coil, said flexible local RF coil element having opposite sides; two mountings respectively mounting said opposite sides of said local RF coil, element to said interior chamber wall; and
   a guide built into said interior chamber wall and interacting with at least one of said mountings to guide said at least one of said mountings along said interior chamber wall to move said local RF coil element from a retracted position adjacent said interior chamber wall to a deployed position adjacent to a patient on the patient bed.

2. A magnetic resonance system as claimed in claim 1 comprising two guides respectively interacting with said two mounting to respectively guide each of said two mountings along said interior chamber wall.

3. A magnetic resonance system as claimed in claim 2 comprising a coupling that synchronizes respective movement of said two mountings in said two guides along said interior chamber wall.

4. A magnetic resonance system as claimed in claim 1 wherein said guide is a linear guide.

5. A magnetic resonance system as claimed in claim 4 comprising a motor mechanically connected to said at least one of said mountings for motorized guidance of said at least one of said mountings in said guide along said interior wall of said chamber.

6. A magnetic resonance system as claimed in claim 4 comprising a plurality of latching positions distributed along a length of said linear guide interacting with said at least one of said mountings to lock said at least one of said mountings at respective positions along said linear guide.

7. A magnetic resonance system as claimed in claim 1 wherein said local coil element is pre-tensioned to automatically lie adjacent said interior wall of said chamber in said retracted position.

8. A magnetic resonance system as claimed in claim 1 wherein said local coil element is at least partially comprised of transparent material.

9. A magnetic resonance system as claimed in claim 1 wherein said local coil element has at least one opening therein allowing the patient to be seen through said local coil element.

10. A magnetic resonance system as claimed in claim 1 wherein said local coil element is movable in a direction along a longitudinal axis of said data acquisition system.

11. A magnetic resonance system as claimed in claim 1 comprising a plurality of local coil elements, identical to said local coil element, respectively disposed along a longitudinal axis of said data acquisition system.

12. A magnetic resonance system as claimed in claim 1 comprising a permanently installed further local coil unit that is permanently installed in or beneath said patient bed.

13. A magnetic resonance system comprising:
   a magnetic resonance data acquisition unit configured to interact with a patient to acquire magnetic resonance data therefrom, said data acquisition unit having a chamber therein in which a patient bed is disposed, said patient bed being configured to have a patient lie thereon;
   a flexible local RF coil element comprising at least one local RF coil, said local RF coil element having a first end and a second end and said first end of said local RF coil element being attached below or at a side of said patient bed and said second end of said local element being extendable from a storage position at said side of or below said patient bed, against a return force urging said local element into said storage position, to a deployed position on said patient.

14. A magnetic resonance system as claimed in claim 13 comprising a return element connected to said local coil element that exerts said return force on said local coil element.

15. A magnetic resonance system as claimed in claim 14 wherein said return element is an element selected from the group consisting of a spring, a pneumatic cylinder, a hydraulic cylinder, and an electrically operable element.

16. A magnetic resonance system as claimed in claim 13 comprising a holder disposed at said side of or below said patient bed, said holder containing said local coil element in said storage position.

17. A magnetic resonance system as claimed in claim 16 wherein said local coil element is rolled up in said holder when in said storage position.

18. A magnetic resonance system as claimed in claim 16 wherein said holder is disposed under said patient bed, and wherein said local coil element is extended in said holder in said storage position under said patient bed.

19. A magnetic resonance system as claimed in claim 13 comprising an attachment element at said second end of said local coil element that attaches said second end of said local coil element to said patient bed when said local coil element is in said deployed position.

20. A magnetic resonance system as claimed in claim 19 wherein said attachment element is an element selected from the group consisting of a latch, a hook-and-loop fastener, a magnetic holder, and a hook.

21. A magnetic resonance system as claimed in claim 13 wherein said local coil element is a first local coil element and wherein said storage position is a first storage position, and comprising a second local coil element having first and second ends, said first end of said second local coil element being attached at another side or under said patient bed and said second end of said second local coil element being movable against a return force to move said second local coil element from a second storage position at said another side of or under said patient bed to a deployed position on the patient, with said second end of said first local coil element and said second end of said second local coil element being connected to each other when each of the first and second local coil elements are in their respective deployed positions.

22. A magnetic resonance system as claimed in claim 13 wherein said local coil element is at least partially comprised of transparent material.

23. A magnetic resonance system as claimed in claim 13 wherein said local coil element has at least one opening therein allowing the patient to be seen through said local coil element.

24. A magnetic resonance system as claimed in claim 13 wherein said local coil element is movable in a direction along a longitudinal axis of said data acquisition system.

25. A magnetic resonance system as claimed in claim 13 comprising a plurality of local coil elements, identical to said local coil element, respectively disposed along a longitudinal axis of said data acquisition system.

26. A magnetic resonance system as claimed in claim 13 comprising a permanently installed further local coil unit that is permanently installed in or beneath said patient bed.

27. A magnetic resonance system as claimed in claim 13 comprising a damping element that damps return movement of said local coil element, against said return force, when said local coil element is moving from said deployed position to said storage position.

28. A magnetic resonance system as claimed in claim 27 wherein said damping element comprises at least one breaking element that mechanically interacts with said local coil element as said local coil element moves from said deployed position to said storage position.

* * * * *